(12) United States Patent
Azam et al.

(10) Patent No.: US 11,420,914 B2
(45) Date of Patent: Aug. 23, 2022

(54) CATALYST COMPOSITION AND PROCESS FOR PREPARING LINEAR ALPHA OLEFINS

(71) Applicant: SABIC GLOBAL TECHNOLOGIES B.V., Bergen Op Zoom (NL)

(72) Inventors: Shahid Azam, Riyadh (SA); Bander Bawareth, Riyadh (SA); Mohammed H. Al-Hazmi, Riyadh (SA); Dafer M. Alshahrani, Riyadh (SA)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 154 days.

(21) Appl. No.: 16/809,761

(22) Filed: Mar. 5, 2020

(65) Prior Publication Data

US 2020/0199039 A1 Jun. 25, 2020

Related U.S. Application Data

(62) Division of application No. 15/326,724, filed as application No. PCT/IB2015/055333 on Jul. 14, 2015, now Pat. No. 10,626,063.

(Continued)

(51) Int. Cl.
*B01J 31/02* (2006.01)
*B01J 31/12* (2006.01)
(Continued)

(52) U.S. Cl.
CPC ............ *C07C 2/26* (2013.01); *B01J 31/0212* (2013.01); *B01J 31/128* (2013.01); *B01J 31/143* (2013.01);
(Continued)

(58) Field of Classification Search
CPC ......... C07C 2/26; C07C 2/02; C07C 2531/14; C07C 2531/04
See application file for complete search history.

(56) References Cited

U.S. PATENT DOCUMENTS

| 4,783,573 A | 11/1988 | Shiraki et al. |
| 5,292,979 A | 3/1994 | Chauvin et al. |

(Continued)

FOREIGN PATENT DOCUMENTS

| CN | 101888902 | 11/2010 |
| DE | 4338414 | 3/1995 |

(Continued)

OTHER PUBLICATIONS

Office Action issued in Corresponding Chinese Application No. 201580038878.7, dated May 8, 2021 (No. English translation provided).

(Continued)

*Primary Examiner* — Youngsul Jeong
(74) *Attorney, Agent, or Firm* — Norton Rose Fulbright US LLP

(57) ABSTRACT

The present disclosure relates to a catalyst composition for the oligomerization of ethylene comprising a zirconium-containing catalyst and an organoaluminum-containing co-catalyst. The disclosure also relates to a process for oligomerization of ethylene in the presence of the catalyst composition according to the disclosure. The disclosed process results in $C_4$-$C_{20}$ linear alpha olefins having improved linearity.

17 Claims, 1 Drawing Sheet

Related U.S. Application Data

(60) Provisional application No. 62/026,123, filed on Jul. 18, 2014.

(51) Int. Cl.
    *C07C 2/26*    (2006.01)
    *B01J 31/14*    (2006.01)
    *B01J 35/00*    (2006.01)

(52) U.S. Cl.
    CPC ........ *B01J 35/0006* (2013.01); *B01J 2231/20* (2013.01); *B01J 2531/004* (2013.01); *C07C 2531/04* (2013.01); *C07C 2531/14* (2013.01)

(56) References Cited

U.S. PATENT DOCUMENTS

| | | | |
|---|---|---|---|
| 5,345,023 | A | 9/1994 | Chauvin et al. |
| 5,496,783 | A | 3/1996 | Chauvin et al. |
| 5,856,612 | A | 1/1999 | Araki et al. |
| 6,221,986 | B1 | 4/2001 | Commereuc et al. |
| 7,566,679 | B2 | 7/2009 | Bolt et al. |
| 8,058,369 | B2 | 11/2011 | Schneider et al. |
| 8,198,497 | B2 | 6/2012 | Biagini et al. |
| 8,481,444 | B2 | 7/2013 | Aliyev et al. |
| 8,524,845 | B2 | 9/2013 | Aliyev et al. |
| 8,653,316 | B2 | 2/2014 | Aliyev et al. |
| 10,626,063 | B2 * | 4/2020 | Azam .................. C07C 2/26 |
| 2003/0216525 | A1 * | 11/2003 | McDaniel ............. C08F 110/02 526/64 |
| 2010/0152398 | A1 * | 6/2010 | Aliyev .................. C07C 2/32 526/172 |
| 2010/0191029 | A1 | 7/2010 | Fritz et al. |
| 2011/0054130 | A1 * | 3/2011 | Aliyev .................. C07C 2/32 526/172 |
| 2011/0282119 | A1 | 11/2011 | Berard et al. |

FOREIGN PATENT DOCUMENTS

| | | | |
|---|---|---|---|
| DE | 4338416 | 4/1995 | |
| DE | 19807226 | 10/1998 | |
| DE | 19812066 | 1/1999 | |
| EP | 1754694 A1 * | 2/2007 | ............ C07C 2/08 |
| EP | 1759766 A1 | 3/2007 | |
| FR | 2689500 A1 | 10/1993 | |
| JP | H08259472 A | 10/1996 | |
| WO | 2009071164 A1 | 6/2009 | |

OTHER PUBLICATIONS

French Patent No. 2689500; Date of Publication: Oct. 8, 1993; Abstract Only, 2 pages.
International Search Report for International Application No. PCT/IB2015/055333; dated Dec. 1, 2015; 5 pages.
Japanese Patent No. 08259472; Date of Publication: Oct. 8, 1996; Abstract Only, 1 page.
Written Opinion of the International Search Report for International Application No. PCT/IB2015/055333; dated Dec. 1, 2015; 5 pages.

* cited by examiner

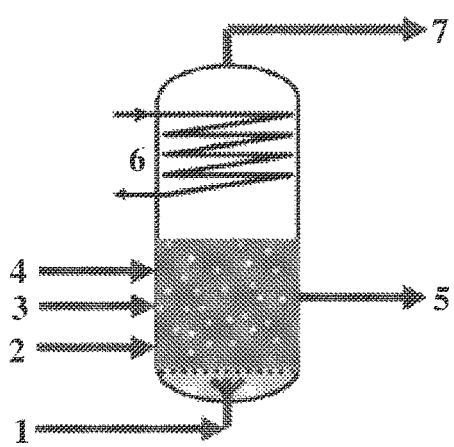

CATALYST COMPOSITION AND PROCESS FOR PREPARING LINEAR ALPHA OLEFINS

CROSS REFERENCE TO RELATED APPLICATIONS

This application is a divisional application of U.S. application Ser. No. 15/326,724, filed Jan. 17, 2017 which is a 371 of International Application No. PCT/IB32015/055333, filed Jul. 14, 2015, which claims priority to U.S. Application No. 62/026,123 filed Jul. 18, 2014, all of which are incorporated herein by reference in their entirety.

TECHNICAL FIELD

Disclosed herein is a catalyst composition comprising a catalyst and a co-catalyst, specifically a zirconium-containing catalyst and an organoaluminum co-catalyst. Also disclosed is a process for oligomerization of ethylene using the catalyst composition, and the linear alpha olefins prepared thereby.

BACKGROUND

Linear alpha olefins (LAOs) are olefins with a chemical formula $C_xH_{2x}$, distinguished from other mono-olefins with a similar molecular formula by linearity of the hydrocarbon chain and the position of the double bond at the primary or alpha position. Linear alpha olefins comprise a class of industrially important alpha-olefins, including 1-butene, 1-hexene, 1-octene, 1-decene, 1-dodecene, 1-tetradecene, 1-hexadecene, 1-octadecene and higher blends of $C_{20}$-$C_{24}$, $C_{24}$-$C_{30}$, and $C_{20}$-$C_{30}$ olefins. Linear alpha olefins are very useful intermediates for the manufacture of detergents, synthetic lubricants, copolymers, plasticizers, and many other important products. Existing processes for the production of linear alpha olefins typically rely on the oligomerization of ethylene.

Linear alpha olefins can be prepared by the catalytic oligomerization of ethylene in the presence of a Ziegler-Natta-type catalyst. Important considerations of the ethylene oligomerization are the desired selectivity and the desired product distribution. The applied catalyst and the process conditions are essential features to obtain the desired characteristics. Various types of catalysts have been applied in the process for the oligomerization of ethylene, including titanium and zirconium-containing catalyst systems. The main disadvantages of such catalysts include poor solubility, harsh operating conditions, and low catalyst selectivity. During the oligomerization process there can be significant amounts of undesirable wax and polymer formation in the presence of these catalysts.

An intrinsic problem of all of these metal-catalyzed ethylene oligomerization processes is the production of linear alpha olefin mixtures of chain length 4, 6, 8, and so on, which can be difficult to separate and whose composition often does not match market demands. This is due to a chemical mechanism which is widely governed by competing chain growth and displacement reaction steps, leading to a Schulz-Flory or Poisson product distribution.

There is an active interest to overcome the above-described technical limitations, to transform the non-selective ethylene oligomerization reactions into more selective processes, and to provide oligomerization catalysts having increased catalytic activity. Accordingly, there remains a need for an improved process for the oligomerization of ethylene to produce linear alpha olefins having improved linearity to meet increased market demands.

BRIEF DESCRIPTION

A catalyst composition for the oligomerization of ethylene comprising: a catalyst; and a co-catalyst; wherein the co-catalyst comprises ethylaluminum sesquichloride and diethyl aluminum chloride.

A process for the oligomerization of an olefin comprising: feeding the olefin, solvent, and a catalyst composition into a reactor; and oligomerizing the olefin in the reactor to form a reaction product comprising linear alpha olefins; wherein the catalyst composition comprises a catalyst and a co-catalyst; wherein the co-catalyst comprises ethylaluminum sesquichloride and diethyl aluminum chloride.

An olefin oligomerization reaction comprising a catalyst composition comprising a zirconium-based catalyst, and an at least two co-catalyst combination, wherein catalytic activity of the catalyst composition is increased by about 92% in comparison to a catalyst composition comprising the zirconium-based catalyst and one co-catalyst of the at least two co-catalyst combination.

An olefin oligomerization reaction comprising a catalyst composition comprising a zirconium-based catalyst, and an at least two co-catalyst combination resulting in a linear alpha olefin composition comprising C4, C6, and C8 linear olefin fractions, wherein purity of the C4 fraction is at least about 99%.

A linear alpha olefin composition resulting from an oligomerization reaction comprising C4-C14 linear olefin fractions, wherein purity of the C4-C14 fractions is at least about 90%.

The above described and other features are exemplified by the following FIGURE and detailed description.

BRIEF DESCRIPTION OF THE DRAWINGS

The following FIGURE is an exemplary embodiment.

FIG. 1 shows a schematic representation of the oligomerization of ethylene in a bubble column reactor.

DETAILED DESCRIPTION

Described herein is a catalyst composition and process for the production of linear alpha olefins, as well as linear alpha olefins produced from the catalyst composition. It was unexpectedly discovered that the use of a mixed co-catalyst comprising ethylaluminum sesquichloride (EASC) and diethyl aluminum chloride (DEAC) in the oligomerization of ethylene can provide linear alpha olefins having improved linearity as compared to linear alpha olefins made without the use of the mixed co-catalyst described herein (e.g., linear alpha olefins made with EASC or DEAC). For example, the purity of C8+ linear alpha olefin fractions can be significantly improved. Furthermore, the co-catalyst mixture can result in increased catalyst activity. Additionally, the co-catalyst mixture can result in improved linear alpha olefin linearity at lower operating temperatures.

The linear alpha olefins made by the process disclosed herein can generally be addition products containing greater than or equal to two ethylene units, but not as many ethylene units as in the relatively high molecular weight addition product referred to as polyethylene. The method of the present application can be adapted for production of linear mono-olefinic oligomers, for example, alpha-olefins having 4 to 20 carbon atoms.

The catalyst composition of the present disclosure can comprise two components, namely a catalyst and a co-catalyst. The catalyst composition of the present disclosure can consist of a catalyst and a co-catalyst. The catalyst composition of the present disclosure can consist essentially of a catalyst and a co-catalyst. The catalyst can comprise a transition metal compound, for example, the catalyst can be a zirconium-containing catalyst. The zirconium-containing catalyst can be a zirconium carboxylate having the formula $Zr(OOCR)_mX_{4-m}$, where R is alkyl, alkenyl, aryl, aralkyl or cycloalkyl, X is halide, for example X is chlorine or bromine, and m is 0 to 4. For example, R can be an alkyl group having 1 to 20 carbon atoms, for example, 1 to 5 carbon atoms. For example, the catalyst can be zirconium tetraisobutyrate.

The second component of the catalyst composition can be a co-catalyst. The co-catalyst can be an organoaluminum compound, for example, an alkyl aluminum halide. The co-catalyst can comprise ethylaluminum sesquichloride (EASC), diethyl aluminum chloride (DEAC), or a combination comprising at least one of the foregoing. For example, the co-catalyst can be a mixture comprising ethylaluminum sesquichloride and diethyl aluminum chloride. For example, the co-catalyst can be a mixture consisting of ethylaluminum sesquichloride and diethyl aluminum chloride. As used herein, the term "mixture" generally refers to a combination of the recited components. For example, a co-catalyst mixture comprising ethylaluminum sesquichloride and diethyl aluminum chloride refers to a co-catalyst comprising a combination of ethylaluminum sesquichloride and diethyl aluminum chloride. When a co-catalyst mixture comprising ethylaluminum sesquichloride and diethyl aluminum chloride is used, the relative amounts of EASC:DEAC can vary. For example, the ratio of EASC:DEAC can be 1:1 to 10:1, for example, the ratio of EASC:DEAC can be 1:1, for example, the ratio of EASC:DEAC can be 3:1, for example, the ratio of EASC:DEAC can be 6:1, for example, the ratio of EASC:DEAC can be 9:1.

In an embodiment, the catalyst composition of the present disclosure can exclude any additional components. For example, the catalyst composition can exclude organic compounds or additives.

The catalyst composition disclosed herein can be prepared by dissolving the components in aromatic, halide aromatic, and/or aliphatic solvents. For preparing the catalyst composition, there is no particular limitation on the order of addition of the catalyst components. The resulting catalyst composition used for the production of linear alpha-olefins can be dissolved in an inert organic solvent.

Examples of desirable organic solvents can include, but are not limited to, aromatic hydrocarbon solvents which can be unsubstituted or substituted with halogens, for example, toluene, benzene, xylene, monochlorobenzene, dichlorobenzene, chlorotoluene, aliphatic paraffin hydrocarbons, for example, pentane, hexane, heptane, octane, nonane, decane, alicyclic hydrocarbon compounds, for example, cyclohexane, decahydronaphthalene, and halogenated alkanes, for example, dichloroethane and dichlorobutane.

The relative amounts of the catalyst and the co-catalyst comprising the catalyst composition can be varied. For example, the ratio of Al:Zr can be 1:1 to 50:1, for example, the ratio of Al:Zr can be 10:1, for example, the ratio of Al:Zr can be 20:1, for example, the ratio of Al:Zr can be 25:1, for example, the ratio of Al:Zr can be 35:1, for example, the ratio of Al:Zr can be 40:1.

The present disclosure is further directed to a process for the oligomerization of ethylene wherein ethylene can be contacted in a reactor with the above-described catalyst composition to produce linear alpha olefins. The linear alpha olefins produced can have increased linearity. As used herein, the term "linearity" as it relates to linear alpha olefins is equivalent to "purity". For example, the linearity of the linear alpha olefins can be increased by greater than or equal to 1.5% for C8+ linear alpha olefins as compared to a different catalyst composition used to produce linear alpha olefins, for example, greater than or equal to 6%, for example, greater than or equal to 10%, for example, greater than or equal to 50%, for example, greater than or equal to 80%, for example, greater than or equal to 90%.

The above described catalyst composition can further have increased activity in the oligomerization process. For example, the activity of the catalyst composition can be increased by greater than or equal to 50% as compared to a different catalyst composition used to produce linear alpha olefins, for example, greater than or equal to 60%, for example, greater than or equal to 75%, for example, greater than or equal to 85%, for example, greater than or equal to 90%, for example greater than or equal to 92%, for example, greater than or equal to 95%. Unexpectedly, the activity of the catalyst composition can also be increased at temperatures lower than those required for a different catalyst composition used to produce linear alpha olefins. For example, the activity can be increased by greater than or equal to 10%, for example, greater than or equal to 20%, for example, greater than or equal to 25%, for example, greater than or equal to 26% at a temperature lower than that required for a different catalyst composition.

An oligomerization reaction can comprise a catalyst composition comprising a zirconium-based catalyst and an at least two catalyst combination, wherein catalytic activity of the catalyst composition can be increased by about 92% in comparison to a catalyst composition comprising the zirconium-based catalyst and one co-catalyst of the at least two co-catalyst combination. The at least two co-catalyst combination can include ethylaluminum sesquichloride and diethyl aluminum chloride. The olefin can be ethylene. A linear alpha olefin composition can result from the olefin oligomerization reaction where the purity of the C4 fraction can be at least about 99%, for example, the purity of the C6 fraction can be at least about 98%, for example, the purity of the C8 fraction can be at least about 96%.

An olefin oligomerization reaction can comprise a catalyst composition comprising a zirconium-based catalyst, and an at least two co-catalyst combination, resulting in a linear alpha olefin composition comprising C4, C6, and C8 linear alpha olefin fractions, where purity of the C4 fraction can be at least about 99%, for example, the purity of the C6 faction can be at least about 98%, for example, the purity of the C8 fraction can be at least about 96%. The at least two co-catalyst combination can comprise sesquichloride and diethyl aluminum chloride. A linear alpha olefin can result from an oligomerization reaction comprising C4 to C14 linear olefin fractions, where purity of the C4 to C14 fractions is at least about 90%, for example, the purity of the C4 fraction can be at least about 99%. A polyethylene polymer composition can result from the linear alpha olefin composition.

Oligomerization can occur at temperatures of 10 to 200° C., for example, 20 to 100° C., for example, 50 to 90° C., for example, 55 to 80° C., for example, 60 to 70° C. Operating pressures can be 1 to 5 MegaPascals (MPa), for example, 2 to 4 MPa. The process can be continuous and mean residence times can be 10 minutes to 20 hours, for example 30 minutes to 4 hours, for example, 1 to 2 hours. Residence times can be chosen so as to achieve the desired conversion at high selectivity.

The process can be conducted in solution using an inert solvent which can desirably be non-reactive with the catalyst composition. Alternatively, the process can be conducted in the presence of a solvent comprising a liquid alpha olefin, for example, $C_6$-$C_{100}$ alpha olefins. Solvents for use in the process can include, but are not limited to, aromatic or aliphatic hydrocarbons and halogenated aromatics such as chlorobenzene, dichlorobenzene, chlorotoluene, and combinations comprising at least one of the foregoing. For example, the solvents can include toluene, xylenes, $C_3$-$C_{24}$ alkanes, and combinations comprising at least one of the foregoing. For example, the solvent can be toluene.

The process can be carried out in any reactor, for example, a loop reactor, a plug-flow reactor, or a bubble column reactor. Oligomerization of ethylene is an exothermic reaction that can be cooled by a surplus flow of ethylene. A multipoint temperature measurement within the two-phase level can allow for detection of a thermal gradient. The gases leaving at a top portion of the reactor can be cooled using a series of external coolers and condensers. The gas phase, after further cooling, can be recycled.

A bottom stream leaving the oligomerization reactor from a bottom portion can contain the active catalyst and unreacted ethylene. The reaction can be terminated to avoid undesirable side reactions by removing catalyst components from the organic phase through extraction with a caustic aqueous phase. Contact with the caustic aqueous phase can result in formation of nonreactive minerals corresponding to the catalyst components.

The organic phase, after passage through the catalyst removal system, can pass through a molecular sieve absorption bed and can then be fed to a distillation column to recover dissolved ethylene. Recovered ethylene can be recycled via an ethylene recycle loop while the product is fed to an intermediate vessel, after which the product can be fed to a separation section.

In an embodiment, the oligomerization process can be carried out in a bubble column reactor. FIG. 1 depicts the oligomerization process utilizing a bubble column reactor. Ethylene (1) can be introduced to a bubble column reactor via a gas distribution system attached to a bottom section of the bubble column reactor. The liquid heavy linear alpha olefins (4), together with the solvent (2) and the catalyst (3), can be withdrawn from the bottom section of the bubble column reactor (5). As mentioned, the oligomerization reaction is highly exothermic. Advantageously, ethylene can be used as both a reaction feed and a cooling medium in a bubble column reactor. By removing the heat with the ethylene, heat exchanger surfaces within the reaction area, which would be subject to heavy fouling, can be avoided. A part of the formed linear alpha olefins, which are gaseous under reaction conditions, can be condensed at a top portion of the reactor and can serve as reflux for cooling purposes (6), taking advantage of the respective heat of evaporation. Gaseous ethylene and light linear alpha olefins can be removed at the top of the bubble column reactor (7).

The linear alpha olefin product can be isolated using procedures including aqueous caustic catalyst quench followed by water washing and final product recovery by distillation. For example, the liquid product including the solvent (e.g., toluene) with the dissolved ethylene can be fed to a separation section. In a first column, the unconsumed ethylene can be separated from the linear alpha olefin product and the solvent. The ethylene can be recycled back to the reactor. The heavier fractions can be routed to the subsequent separation section where the heavier fractions can be divided into the different linear alpha olefin fractions (e.g., C8, C10, >C12). The solvent can be recovered and also recycled back to the reactor.

The amount of catalyst used in the present process relative to the ethylene feedstock can be expressed as the weight ratio of ethylene feedstock to zirconium. Generally, the amount can be 10,000 to 120,000 grams of ethylene per gram of zirconium present in the catalyst composition, for example, 15,000 to 100,000 grams of ethylene per gram of zirconium, for example 20,000 to 50,000 grams of ethylene per gram of zirconium, for example, 25,000 to 35,000 grams of ethylene per gram of zirconium, for example, 31,000 grams of ethylene per gram of zirconium. These amounts can be determined by processing concerns such as catalyst removal from product, catalyst cost, and the need to minimize the amount of water which will be present.

The presence of water in the system should desirably be minimized during the process disclosed herein because the catalyst can be sensitive to the presence of water. Minor amounts of water can produce undesirable quantities of high molecular weight polyethylene and can therefore, reduce conversions to the desired linear alpha olefin oligomer product.

The feedstock used can be pure ethylene or mixtures of ethylene with inert gases. Optionally, very minor proportions of other olefins can be present, but these can cause the production of unwanted olefin copolymers with attendant loss of conversion and linearity.

The present disclosure is further directed to a polyethylene product comprising linear alpha olefins made by the above-described process. For example, a polyethylene can be derived from the linear alpha olefin product made by the disclosed process. Alpha olefins of high purity are particularly valuable in the production of polyethylene, for example, linear low density polyethylene. The improved purity and linearity of the linear alpha olefins made by the disclosed process can eliminate problems in polyethylene formation, for example with regard to the presence of branched or internal olefins that can lead to subtle differences in the properties of the resulting polyethylene product, which can generally be undesirable.

The present disclosure provides an improved catalyst composition and a process for production of linear alpha olefins. The co-catalyst mixture of ethylaluminum sesquichloride (EASC) and diethyl aluminum chloride (DEAC) can result in a significant improvement in the linearity of the linear alpha olefin products, and in higher catalyst activity. The disclosed co-catalyst composition and method of producing linear alpha olefins can meet the increasing demands for higher purity linear alpha olefin products for a wide range of applications. Therefore, a substantial improvement in the oligomerization of ethylene to give high purity linear alpha olefin products is provided.

EXAMPLES

In the following examples, the oligomerization of ethylene was carried out in the presence of the specified catalyst for a period of 1-2 hours over a cumulative period of 6 months. Comparative Example 1 (C1) and Examples 1-3 (E1-E3) were carried out in a bubble column reactor having an overall diameter of 0.15 meters (m) and an overall height of 2.0 m. Gaseous ethylene was bubbled through a gas phase distribution plate. The linear alpha olefins were produced by homogenous catalytic ethylene oligomerization in the liquid phase according to the reaction

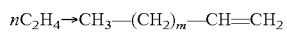

$$nC_2H_4 \rightarrow CH_3-(CH_2)_m-CH=CH_2$$

where m is an odd number.

The oligomerization was catalyzed by a zirconium-containing catalyst (Zr(OOCR)$_4$), specifically zirconium tetraisobutyrate, and a mixed co-catalyst of ethylaluminum sesquichloride (EASC) and diethyl aluminum chloride (DEAC) using an EASC:DEAC ratio of 3:1. As previously described, oligomerization of ethylene is an exothermic reaction cooled by a surplus flow of ethylene. A multipoint temperature measurement within the two-phase level allows for detection of a thermal gradient. The gases leaving the top of the reactor were cooled using a series of external coolers and condensers. The gas phase after further cooling was recycled.

The bottom stream leaving the oligomerization reactor contained the active catalyst and unreacted ethylene. The reaction was terminated to avoid undesirable side reactions by removing catalyst components from the organic phase through extraction with a caustic aqueous phase.

The organic phase, after passage through the catalyst removal system, was passed through a molecular sieve absorption bed and was then fed to a distillation column to recover dissolved ethylene. Recovered ethylene was recycled via the ethylene recycle loop, while the product was fed to an intermediate vessel, and finally to a separation section.

The reactor was operated in a continuous mode to examine the effect of varying co-catalyst composition on linear alpha olefin product linearity at three different temperatures, 60, 70, and 78° C. The aluminum-to-zirconium (Al:Zr) ratio was held constant at 35:1. The catalyst activity and the product distributions for each example are shown in Table 1. Activity was measured in kilograms (kg) of linear alpha olefin produced per gram (g) of zirconium per hour (hr). Product Distribution was measured in weight percent (wt %).

a lower operating temperature (60° C.) can be used to obtain comparable or higher catalyst activity (8.2 kg$_{LAO}$/g$_{Zr}$/hr) when a co-catalyst comprising EASC and DEAC was used. Similarly, Example E2 showed improved catalyst activity of 9.5 kg$_{LAO}$/g$_{Zr}$/hr at 70° C. At 78° C., the same operating temperature as Comparative Example C1, the catalyst activity was nearly doubled (14.4 kg$_{LAO}$/g$_{Zr}$/hr) when the co-catalyst comprising EASC and DEAC was used. Stated another way, the catalyst activity was increased by 92% when the co-catalyst comprising EASC and DEAC was used at 78° C.

Table 2 shows the purity of the linear alpha olefins fractions for each of the examples, and further compares the bubble column reactor plant data to commercial plant data. The data in Table 2 demonstrates that the modified co-catalyst comprising EASC and DEAC can significantly improve the linearity of LAO fractions.

TABLE 2

| | Product purity (%) | | | |
|---|---|---|---|---|
| | Commercial | Bubble Column Plant Tests | | |
| | Plant Current Specs @ 78° C. Using EASC | C1 EASC @ 78° C. | E1 EASC + DEAC @ 60° C. | E2 EASC + DEAC @ 70° C. | E3 EASC + DEAC @ 78° C. |
| C4 | >99 | 98.24 | 99.49 | 99.25 | 99.74 |
| C6 | >98 | 97.46 | 98.66 | 98.49 | 98.45 |
| C8 | >95 | 95.08 | 97.36 | 96.79 | 97.08 |
| C10 | >86 | 86.71 | 94.60 | 93.76 | 93.16 |
| C12 | >86 | 79.47 | 92.91 | 91.19 | 92.42 |
| C14 | >78 | 78.89 | 91.15 | 88.19 | 87.96 |
| C16 | | 78.73 | 88.93 | 85.62 | 86.27 |
| C18 | | 76.87 | 86.84 | 81.94 | 83.60 |
| C20 | 75.6 | 44.76 | 85.94 | 80.56 | 81.52 |

The linearity of C8+ linear alpha olefin fractions was observed to improve when employing the co-catalyst comprising EASC and DEAC, with an especially notable

TABLE 1

Catalyst activity and product distribution at Al:Zr ratio 35:1

| Examples | Reaction temperature (Co-catalyst) | Activity (kg$_{LAO}$/g$_{Zr}$/hr) | Product Distribution wt % | | | | | | | |
| | | | C4 | C6 | C8 | C10 | C12 | C14 | C16 | C18 | C20+ |
|---|---|---|---|---|---|---|---|---|---|---|---|
| C1 | 78° C. (EASC) | 7.5 | 23.5 | 22.3 | 18.1 | 11.7 | 8.1 | 5.9 | 4.0 | 2.5 | 3.7 |
| E1 | 60° C. (EASC + DEAC) | 8.2 | 32.8 | 22.1 | 20.9 | 8.4 | 5.8 | 4.1 | 2.8 | 1.9 | 1.2 |
| E2 | 70° C. (EASC + DEAC) | 9.5 | 31.7 | 21.7 | 20.1 | 9.3 | 6.5 | 4.4 | 3.1 | 2.0 | 1.2 |
| E3 | 78° C. (EASC + DEAC) | 14.4 | 24.5 | 17.5 | 17.1 | 11.7 | 9.3 | 7.3 | 5.5 | 4.1 | 3.0 |

Comparative Example 1 (C1) mimics conditions of a commercial reactor, employing only EASC as the co-catalyst at a temperature of 78° C. Examples 1-3 use a co-catalyst comprising EASC and DEAC, and demonstrate the effect of variable operating temperatures. The catalyst activity increased when the co-catalyst comprising EASC and DEAC was employed, showing a dependence on temperature. The catalyst activity determined for comparative example C1 was 7.5 kg$_{LAO}$/g$_{Zr}$/hr. Example E1 showed that improvement in linearity seen in C10+ linear alpha olefin fractions. Example E1 shows that linearity of C8-C18 fractions can be increased by about 2 to about 17%, and the linearity of C10-C18 fractions can be increased by about 9 to about 17% at a temperature of 60° C., compared to corresponding linearities obtained for Comparative Example C1 (e.g., using a different catalyst composition for oligomerization of ethylene). The C4-C20 linear alpha olefins of Example E1 had an average linearity of 92.8%, and the C4-C20 linear alpha olefins of Comparative Example C1 had an average linearity of 81.8%. Example E2 shows that linearity of C8-18 fractions can be increased by about 2 to about 15%, and the linearity of C10-C18 fractions can be increased by about 6.5 to about 15% at a temperature of 70° C., compared to Comparative Example C1. The C4-C20 linear alpha olefins of Example E2 had an average linearity of 90.6%. Example E3 shows that linearity of C8-C18 fractions can be increased by about 2 to about 16.5%, and the linearity of C10-C18 fractions can be increased by about 6.5 to about 16.5% at a temperature of 78° C., compared to Comparative Example C1. The C4-C20 linear alpha olefins of Example E3 had an average linearity of 91.1%. Interestingly, the linearity of the C20 fractions increased dramatically, by about 80 to about 92% when employing the co-catalyst mixture comprising EASC and DEAC, compared to the linearity of the C20 fraction of Comparative Example C1.

Furthermore, the data shown in Table 2 indicates that the co-catalyst mixture comprising EASC and DEAC can result in improved linearity at operating temperatures that are lower than the operating temperature required when a co-catalyst different from the EASC and DEAC mixture is used. While Examples E1-3 collectively show increased linearity relative to Comparative Example C1, the greatest improvements in linearity were noted at the lowest operating temperature of 60° C. (Example E1).

The catalyst composition and methods of making disclosed herein include at least the following embodiments:

Embodiment 1: A catalyst composition for the oligomerization of ethylene comprising: a catalyst; and a co-catalyst; wherein the co-catalyst comprises ethylaluminum sesquichloride and diethyl aluminum chloride.

Embodiment 2: The catalyst composition of embodiment 1, wherein the catalyst comprises zirconium.

Embodiment 3: The catalyst composition of embodiment 1 or 2, wherein the catalyst is zirconium tetraisobutyrate.

Embodiment 4: The catalyst composition of any of embodiments 1-3, wherein the Al:Zr ratio is 35:1.

Embodiment 5: The catalyst composition of any of embodiments 1-4, wherein the co-catalyst comprises ethylaluminum sesquichloride and diethyl aluminum chloride in a ratio of 3:1.

Embodiment 6: A process for the oligomerization of an olefin comprising: feeding the olefin, solvent, and a catalyst composition into a reactor; and oligomerizing the olefin in the reactor to form a reaction product comprising linear alpha olefins; wherein the catalyst composition comprises a catalyst and a co-catalyst; wherein the co-catalyst comprises ethylaluminum sesquichloride and diethyl aluminum chloride.

Embodiment 7: The process of embodiment 6, wherein the olefin is ethylene.

Embodiment 8: The process of embodiment 6 or 7, wherein the solvent is toluene.

Embodiment 9: The process of any of embodiments 6-8, wherein the catalyst comprises zirconium.

Embodiment 10: The process of any of embodiments 6-9, wherein the catalyst is zirconium tetraisobutyrate.

Embodiment 11: The process of any of embodiments 6-10, wherein the oligomerization is conducted at a temperature of 30 to 120° C.

Embodiment 12: The process of any of embodiments 6-11, wherein the reactor is a bubble column reactor.

Embodiment 13: The process of any of embodiments 6-12, wherein the catalyst composition has a catalytic activity 10% greater than a different catalyst composition used for oligomerization of an olefin.

Embodiment 14: The process of any of embodiments 6-13, wherein the catalyst composition has a catalytic activity 26% greater than a different catalyst composition used for oligomerization of an olefin.

Embodiment 15: The process of any of embodiments 6-14, wherein the catalyst composition has a catalytic activity 92% greater than a different catalyst composition used for oligomerization of an olefin.

Embodiment 16: The process of any of embodiments 6-15, wherein the linear alpha olefin reaction product comprises C8+ fractions, having greater than or equal to a 2% increase in linearity compared to a different catalyst composition used for oligomerization of an olefin.

Embodiment 17: The process of embodiment 16, wherein the C8+ fractions have greater than or equal to a 6% increase in linearity compared to a different catalyst composition used for oligomerization of an olefin.

Embodiment 18: The process of embodiment 16 or 17, wherein the C8+ fractions have greater than or equal to a 10% increase in linearity compared to a different catalyst composition used for oligomerization of an olefin.

Embodiment 19: A linear alpha olefin composition made by the process of any of embodiments 6-18 comprising C4-C14 fractions having a linearity of at least 90%.

Embodiment 20: A C4 linear alpha olefin made by the process of any of embodiments 6-19 having a linearity of at least 99%.

Embodiment 21: A C6 linear alpha olefin made by the process of any of embodiments 6-19 having a linearity of at least 98%.

Embodiment 22: A C8 linear alpha olefin made by the process of any of embodiments 6-19 having a linearity of at least 96%.

Embodiment 23: A C10+ linear alpha olefin made by the process of any of embodiments 6-19 having a linearity of at least 80%.

Embodiment 24: A polyethylene composition, wherein the polyethylene is derived from at least one linear alpha olefin made by the process of any of embodiments 6-23.

Embodiment 25: An olefin oligomerization reaction comprising a catalyst composition comprising a zirconium-based catalyst, and an at least two co-catalyst combination, wherein catalytic activity of the catalyst composition is increased by about 92% in comparison to a catalyst composition comprising the zirconium-based catalyst and one co-catalyst of the at least two co-catalyst combination.

Embodiment 26: The olefin oligomerization reaction of embodiment 25, wherein the at least two co-catalyst combination comprises ethylaluminum sesquichloride and diethyl aluminum chloride.

Embodiment 27: The olefin oligomerization reaction of any of embodiments 25-26, wherein the olefin is ethylene.

Embodiment 28: The olefin oligomerization reaction any of embodiments 25-27, resulting in a linear alpha olefin composition, wherein purity of a C4 fraction is at least about 99%.

Embodiment 29: The olefin oligomerization reaction of any of embodiments 25-27, resulting in a linear alpha olefin composition, wherein purity of a C6 fraction is at least about 98%.

Embodiment 30: The olefin oligomerization reaction of any of embodiments 25-27, resulting in a linear alpha olefin composition, wherein purity of a C8 fraction is at least 96%.

Embodiment 31: An olefin oligomerization reaction comprising a catalyst composition comprising a zirconium-based catalyst, and an at least two co-catalyst combination resulting in a linear alpha olefin composition comprising C4, C6, and C8 linear olefin fractions, wherein purity of the C4 fraction is at least about 99%.

Embodiment 32: The olefin oligomerization reaction of embodiment 31, wherein purity of the C6 fraction is at least about 98%.

Embodiment 33: The olefin oligomerization reaction of embodiment 31, wherein purity of the C8 fraction is at least about 96%.

Embodiment 34: The olefin oligomerization reaction of any of embodiments 31-33, wherein the at least two co-catalyst combination comprises ethylaluminum sesquichloride and diethyl aluminum chloride.

Embodiment 35: A linear alpha olefin composition resulting from an oligomerization reaction comprising C4-C14 linear olefin fractions, wherein purity of the C4-C14 fractions is at least about 90%.

Embodiment 36: The liner alpha olefin composition of embodiment 35, wherein the purity of the C4 fraction is at least about 99%.

Embodiment 37: A polyethylene polymer composition resulting from the linear alpha olefin composition of embodiment 36.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

The invention claimed is:

1. A catalyst composition for an oligomerization of ethylene comprising:
    a catalyst, wherein the catalyst comprises a zirconium carboxylate having the formula $Zr(OOCR)_m X_{4-m}$; and
    a co-catalyst;
    wherein the co-catalyst comprises ethylaluminum sesquichloride (EASC) and diethyl aluminum chloride (DEAC) in an EASC to DEAC mass ratio of 3:1;
    wherein the Al:Zr molar ratio in the catalyst composition is 35:1; and
    wherein R is alkyl, alkenyl, aryl, aralkyl or cycloalkyl;
    X is a halide; and
    m is 1 to 4.

2. The catalyst composition of claim 1, wherein the catalyst is zirconium tetraisobutyrate.

3. A process of making the catalyst composition of claim 1, the process comprising combining the catalyst with the ethylaluminum sesquichloride (EASC) and the diethyl aluminum chloride (DEAC).

4. The catalyst composition according to claim 1, wherein R is alkyl.

5. The catalyst composition according to claim 1, wherein R is alkenyl.

6. The catalyst composition according to claim 1, wherein R is aryl.

7. The catalyst composition according to claim 1, wherein R is aralkyl.

8. The catalyst composition according to claim 1, wherein R is cycloalkyl.

9. The process according to claim 3, wherein the combining is conducted in the presence of a solvent.

10. The process according to claim 9, wherein the solvent is an aromatic hydrocarbon solvent.

11. The process according to claim 10, wherein the aromatic hydrocarbon solvent is substituted with a halogen.

12. The process according to claim 10, wherein the aromatic hydrocarbon solvent is selected from the group consisting of toluene, benzene, xylene, monochlorobenzene, dichlorobenzene and chlorotoluene.

13. The process according to claim 12, wherein the solvent is toluene.

14. The process according to claim 9, wherein the solvent is an aliphatic paraffin hydrocarbon.

15. The process according to claim 14, wherein the aliphatic paraffin hydrocarbon is selected from the group consisting of pentane, hexane, heptane, octane, nonane and decane.

16. The process according to claim 9, wherein the solvent is an alicyclic hydrocarbon compound.

17. The process according to claim 9, wherein the solvent is a halogenated alkane.

* * * * *